United States Patent [19]

Cameron et al.

[11] Patent Number: 5,025,108

[45] Date of Patent: Jun. 18, 1991

[54] PROCESS FOR PRODUCING OLEFINS FROM NATURAL GAS

[75] Inventors: Charles Cameron, Paris; Hubert Mimoun; Alain Robine, both of Rueil Malmaison; Serge Bonnaudet, Paris; Patrick Chaumette, Bougival; Quang Dang Vu, Neuilly, all of France

[73] Assignee: Institut Francais du Petrole, Rueil-Malmaison, France

[21] Appl. No.: 332,831

[22] Filed: Apr. 4, 1989

[30] Foreign Application Priority Data

Apr. 5, 1988 [FR] France ................................ 88 04588

[51] Int. Cl.$^5$ .............................................. C07C 2/00
[52] U.S. Cl. ...................................... 585/500; 585/601; 585/654; 585/656; 585/658; 585/661; 585/700; 585/943
[58] Field of Search ................ 585/500, 601, 654, 656, 585/658, 661, 700, 943

[56] References Cited

U.S. PATENT DOCUMENTS

| 3,373,218 | 3/1968 | Schuman | 585/650 |
| 4,215,231 | 7/1980 | Raymond | 585/324 |
| 4,620,051 | 10/1986 | Kolts et al. | 585/661 |
| 4,751,336 | 6/1988 | Jezl et al. | 585/700 |
| 4,822,944 | 4/1989 | Brazdil, Jr.; et al. | 585/500 |

OTHER PUBLICATIONS

J. Am. Chem. Soc., vol. 107, No. 18, (1985).
Journal of Catalysis, 100 (1986), pp. 353-359.

*Primary Examiner*—Patrick P. Garvin
*Assistant Examiner*—E. D. Irzinski
*Attorney, Agent, or Firm*—Millen, White & Zelano

[57] ABSTRACT

Process for producing olefins from natural gas. The natural gas is fractionated (1). The methane (3) mixed with oxygen (6) crosses the oxidizing reactor (5), receives the C$_{2+}$ hydrocarbons (7) and the mixture crosses the pyrolysis reactor (8). A hydrocarbons flow containing olefins (10) is collected.

15 Claims, 1 Drawing Sheet

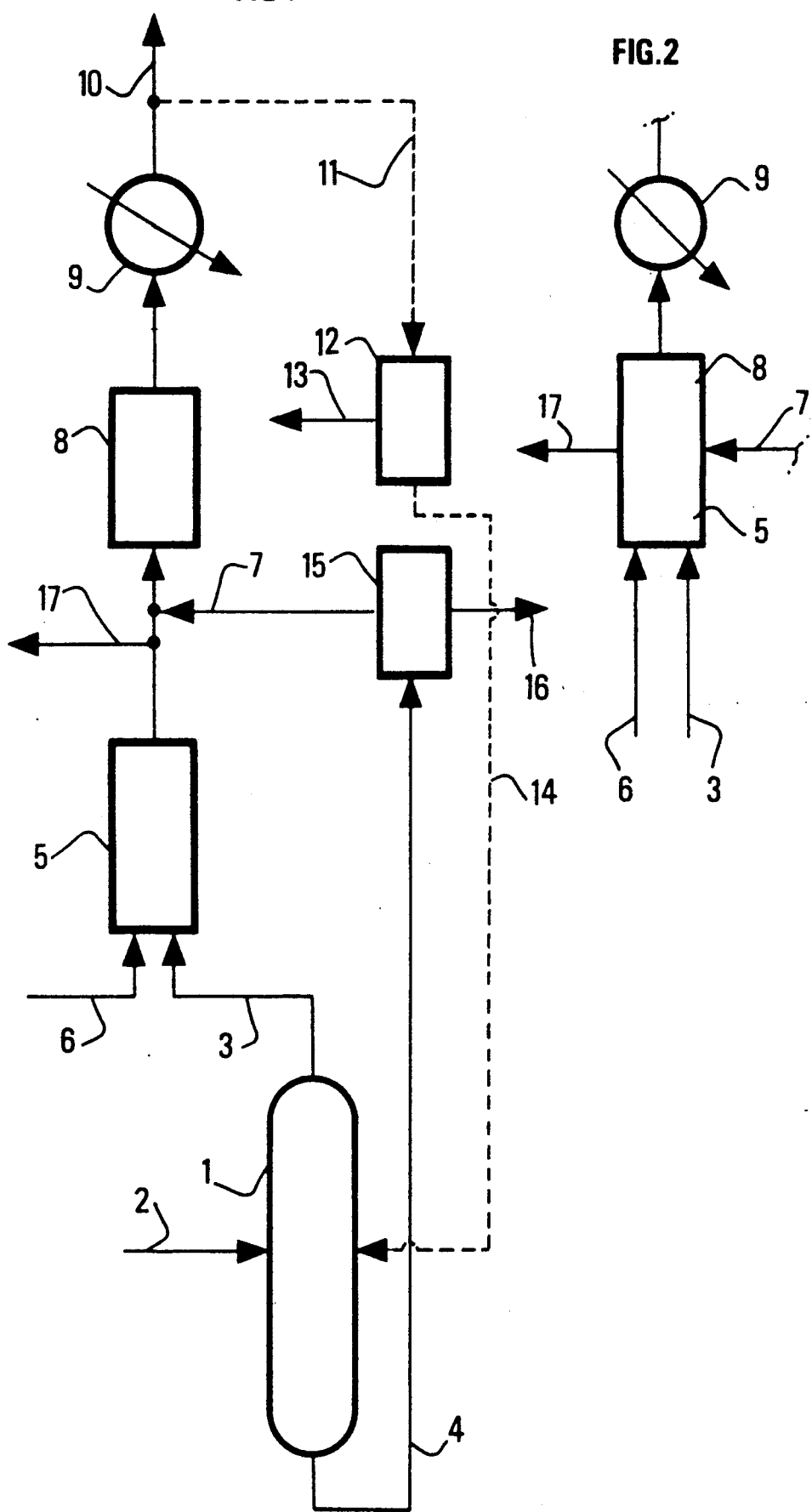

PROCESS FOR PRODUCING OLEFINS FROM NATURAL GAS

BACKGROUND OF THE INVENTION

The present invention relates to a process for producing olefins from natural gas.

Natural gas is an abundant fossil raw material which is essentially composed of methane, the currently proved reserves of which amount to $10^{14}$ m$^3$, which represents about 50 years of world consumption. Gas pools often show large amounts of ethane, propane, other superior alkanes as well as other constituents such as $H_2O$, $CO_2$, $N_2$, $H_2S$ and He. The major part of the propane and other superior alkanes in the natural gas are liquefied and called LPG (liquefied petroleum gas). In pools which are rich in helium (generally more than 0.3% by volume), the helium is separated because of its high commercial value. The hydrogen sulfide is also separated because of its corrosiveness, and water is separated, because of the forming of hydrates which hinder the natural gas transportation. The natural gas obtained is then called a non-condensed gas and it mainly contains (for exemple 55–99% by volume) methane as well as 1 to 25% by volume of ethane and optionally low amounts of propane, nitrogen and/or carbon dioxide.

The major part of the natural gas is used for individual and industrial heating; still, there are some processes for converting natural gas into superior hydrocarbons.

Directly converting natural gas into ethylene would be highly desirable since ethylene can serve as a raw material for numerous syntheses of important products.

Two processes which allow reaching this goal are methane pyrolysis and methane catalytic pyrolysis, but these are very endothermic processes which require very high energy input. Moreover, both processes produce high, undesired amounts of coke.

Ethane pyrolysis is also a well-known, very endothermic process which is therefore a substantial power consumer. But, since ethane pyrolysis is achieved at temperatures that are lower than those used for methane, it is not possible to simultaneously convert these two compounds. So, when one operates at the ethane conversion temperature, the methane which is present in the ethane charge comes out of the reactor essentially unchanged.

Ethylene and other hydrocarbons can also be produced through the oxidizing coupling of methane, either in the sequential or in the simultaneous mode.

The reaction of oxidizing coupling in the sequential mode involves the oxidation of methane by a reducible agent, followed by the re-oxidation of said agent, which is carried out separately, by the oxygen in the air. Several U.S. patents (for example U.S. Pat. Nos. 4,499,323, 4,523,049, 4,547,611, 4,567,307) mention the use of numerous metal oxides, especially Mn, Ce, Pr, Sn, In, Ge, Pb, Sb, Bi, Tb as reducible agents for this reaction.

The reaction of oxidizing coupling in the simultaneous mode (scavenging of a mixture of methane and oxygen on a contact mass C) can be qualitatively expressed as:

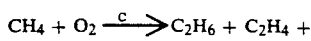
$$CH_4 + O_2 \xrightarrow{C} C_2H_6 + C_2H_4 + \text{other hydrocarbons} + CO + CO_2 + H_2 + H_2O$$

The use of rare-earth oxides, alkaline and alkaline-earth oxides, and titanium, zirconium, hafnium and zinc oxides, alone or mixed, as catalysts for the reaction of oxidizing coupling in the simultaneous mode has been mentioned in several patents (for example European Patent Nos. EP 210,383 A2, EP 189,079 A1, EP 206,044 A1 and World Patent No. WO 86,07351).

Former efforts in the oxidizing coupling of methane have led to the forming of low ethylene/ethane ratios, generally ranging from about 0.8 to 1.2 for $C_2+$ products selectivities higher than about 65%. Such low ethylene/ethane ratios require separating the ethane from the ethylene and carrying out the costly pyrolysis of ethane into ethylene. It should also be known that the former efforts in the oxidizing coupling of methane have not taken into account the other major constituents of natural gas such as ethane, propane and other saturated hydrocarbons. The processes concerning the oxidizing coupling of methane which are described above are not very suitable for the selective conversion of natural gas into olefins because of the presence of significant amounts of light hydrocarbons (such as ethane and propane) in natural gas. The relative oxidation rates of light alkanes under the conditions of oxidizing coupling of methane are about 15 to 100 times higher than those relative to the oxidation of methane, that is to say that the light hydrocarbons are converted into ethylene and carbon oxides before the methane begins to react. So, the former processes cannot be efficiently applied to natural gas.

OBJECT OF THE INVENTION

One object of the present invention is to provide a highly efficient method for producing olefins, in particular ethylene, from natural gas.

Another object of the invention is to provide a method for dehydrogenizing the alkanes that come out of the methane oxidation reactor, without requiring an independent pyrolysis reactor.

SUMMARY OF THE INVENTION

These objectives are reached with the present process for oxy-pyrolyzing natural gas, which comprises the following stages:

(1) separating the natural gas into two fractions: a first methane-enriched gas fraction (which preferably is substantially free from ethane, propane and other hydrocarbons that are present in natural gas) and a second ethane-enriched gas fraction (which may or may not contain other light hydrocarbons and/or non-hydrocarbon gases);

(2) selectively oxidizing the first gas fraction containing methane with molecular oxygen, in the presence of a contact mass, in order to constitute an effluent the main components of which are $C_2$ hydrocarbons and water;

(3) admixing at least the second gas fraction to the effluent of the methane selective oxidation reaction, at a place where at least about 80% by volume of the molecular oxygen introduced at stage (2) has been consumed, and (4) carrying out the controlled pyrolysis of the mixture of said effluent and said second gas fraction, which produces a gaseous mixture that is rich in olefins and in hydrogen.

DETAILED DESCRIPTION OF THE INVENTION

In comparison to the existing processes which employ the oxidizing coupling of methane or the pyrolysis and the catalytic pyrolysis of methane and ethane, the oxypyrolysis process of natural gas according to the invention has the following major advantages:

(a) the heat that is emitted during the oxidation reaction (approximately 250 kJ per mol of methane having been reacted) is immediately used for pyrolyzing the effluent alkanes and the other alkanes that have been added (such as ethane, propane, butane and naphtha);

(b) the olefins (especially ethylene and propylene)/$C_2+$ alkanes (especially ethane and propane) ratios are nearly always higher than 1.5;

(c) appropriate olefins/alkanes ratios can be obtained by controlling the residence time in the pyrolysis stage (4) and the temperature of the gaseous effluent which is affected by the selective oxidation of methane;

(d) the oxidation reaction effluent can serve as a dehydrogenation diluent for a pyrolysis reaction of ethane and other saturated hydrocarbons which can be introduced after the initial oxidation reaction;

(e) the separate conversion of ethane into ethylene through a conventional pyrolysis process is no longer required;

(f) the process allows treating the total natural gas contents and not only the methane which is contained in the natural gas.

Three important elements should be taken into account, so that the process can work in an optimal way; these are: (1) the contact mass, (2) the second gas fraction which contains saturated hydrocarbons and (3) the control of the temperature and the residence time of the mixture of effluent and of gas added between the place where the mixing is achieved and the thermal quenching which is achieved at the reactor outlet.

As for the contact mass used in the selective oxidation reaction of methane into superior hydrocarbons, although any well-known contact mass can be utilized, one will preferably use a contact mass that:

(a) can operate in the normal oxidizing coupling conditions, that is to say at temperatures ranging from about 700° to 950° C., (b) produces $C_2+$ products with a selectivity of at least about 65% for a conversion of about 15% of the methane, and (c) preserves its activity and its selectivity for numerous operating hours.

The contact masses which correspond to the conditions mentioned above and the use of which is therefore preferred are those which generally contain alkali metal oxides and/or carbonates (such as lithium, sodium, potassium, rubidium and cesium), alkaline-earth metal oxides and/or carbonates (such as beryllium, magnesium, calcium, strontium and barium), and rare-earth metal oxides and/or carbonates (such as yttrium, lanthanum, praseodymium, neodymium, samarium, gadolinium, terbium, dysprosium, holmium, erbium, thulium, ytterbium, europium and lutecium), either alone (as in the case of rare earths and alkaline earth metals), or mixed (as in the case of alkaline-earth metals doped with alkali metals and rare-earth metals doped with alkali metals and/or alkaline-earth metals). Other contact masses that correspond to the conditions described above are those which contain titanium, zirconium, hafnium, manganese, cerium, tin, indium, germanium, lead, antimony, zinc and bismuth oxides and/or carbonates, preferably with one or several alkaline metals, alkaline-earth, rare-earth oxides and/or carbonates and silica. The contact masses mentioned above are efficient whether alone or doped with halides.

It is also preferable that the contact masses for the selective oxidation of methane:

(a) be efficient for very short contact times, generally less than about 300 milliseconds;

(b) be able to consume at least about 80% (preferably at least about 95%) by volume of the molecular oxygen in the charge during very short contact times.

The contact masses which are particularly preferred are the following:

(a) Contact masses containing alkaline-earth and rare-earth compounds and approximately corresponding to the following formula:

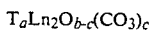

$$T_a Ln_2 O_{b-c}(CO_3)_c$$

where T represents one or several alkaline-earth metals such as beryllium, magnesium, calcium, strontium and baryum, Ln represents one or several rare-earth metals such as yttrium, lanthanum, praseodymium, neodymium, samarium, europium, gadolinium, terbium, dysprosium, holmium, erbium, thulium, ytterbium and lutecium, a=0.001 to 1,000, b=3+a, c=0.1 to b. The rare-earth metals which are preferably used are lanthanum, neodymium and samarium, alone or mixed. The preferred rare-earth metal is lanthanum.

(b) Contact masses containing alkaline-earth, rare-earth and Group IVa compounds and approximately corresponding to the following formula:

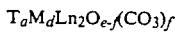

$$T_a M_d Ln_2 O_{e-z}(CO_3)_f$$

where T represents one or several alkaline-earth metals, M represents one or several metals from Group IVa, such as titanium, zirconium and hafnium, Ln represents one or several rare-earth metals, a=0.001 to 1,000, d=0.001 to 2, e=3+a+2d−z, f=0.1 to e, z=0 to 0.5 d. In this formula, z represents a value from 0 to 0.5 d, thus z is equal to 0 when the oxidation state of all the metals from the IVA group is +4, to 0.5 d when the oxidation state of these metals is +3 and ranges from 0 to 0.5 d when there is a mixture of oxidation states +3 and +4 of these metals. The preferred rare-earth metals are lanthanum, neodymium and samarium, and more especially lanthanum.

Contact masses (a) and (b) are not limited to the formulas mentioned above. In fact, the beneficial effect of the presence of rare-earth metals and the alkaline-earth metals and, optionally, of metals from Group IVa, appears whatever the form under which these metals are present, although the oxide and/or carbonate form is the preferred one.

(c) Contact masses containing two or several alkaline-earth metals and approximately corresponding to the following formula:

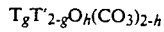

$$T_g T'_{2-g} O_h (CO_3)_{2-h}$$

where T represents one or several alkaline-earth metals which are different from T', such as beryllium, magnesium, calcium, strontium and baryum, T' represents an alkaline-earth metal which is one of the alkaline-earth metals known for forming stable carbonates at high temperatures, such as calcium, strontium and barium, g=0.1 to 1.8, h=0 to 2. The preferred T' alkaline-earth metals are strontium and barium.

Contact masses (c) are not limited to the formula mentioned above. In fact, the beneficial effect of the presence of at least two alkaline-earth metals (where at least one component such as calcium, strontium or barium) appears whatever the form under which these metals are present, although the preferred form is carbonate or oxide and carbonate.

As for the admixed gas (which is rich in ethane, stems at least partially from natural gas and can contain other light hydrocarbons, naphtha and/or non hydrocarbon gases), it has been noticed that adding it to the gas containing methane leads to a low conversion of the methane and to a high conversion of the added hydrocarbons when these total gases are contacted with a gas containing oxygen and a contact mass. Because of the reactivity of ethane (and of the other hydrocarbons in the added gas), which is higher than that of methane, ethane is oxidized into ethylene, CO and $CO_2$ before the methane has sufficiently reacted.

This unsatisfactory way of proceeding is therefore excluded from the present invention, where, on the contrary, said added gas is introduced into the oxypyrolysis reactor after the contact mass bed or at a place where at least about 80% (preferably at least about 95%) of the molecular oxygen has been already consumed during the methane selective oxidation. A certain fraction of the ethane and of the other saturated hydrocarbons of the methane selective oxidation effluent and a certain fraction of the gas containing added hydrocarbons can be dehydrogenized through a pyrolysis reaction in order to form a gas which is rich in olefins, using the heat generated by the methane oxidation reaction and controlling the residence time of the gaseous mixture which is present after the effluent has been mixed with said added gas.

The gas mixture which is subjected to the oxidation (stage 2 of the process) can be used without any diluent or diluted with inert gases such as nitrogen, carbon dioxide or water steam. For safety reasons, the oxygen content in the methane should no exceed 40% by mol; it can thus range from about 0.1 to 40% by mol, preferably from 5 to 25% by mol.

The temperature of the oxy-pyrolysis reaction (stages 2 and 4) generally ranges from 750° to 1,200° C., preferably from 750° to 950° C.

The total pressure (stages 2 and 4) can range for example from 1 to 100 bars, particularly from 1 to 20 bars. The contact time of the methane oxidizing coupling (that is to say the time which is necessary for the consumption of at least about 80% of the molecular oxygen in the charge) ranges from $10^{-6}$ to 1 second, preferably from $10^{-6}$ to $10^{-1}$ second. The residence time of the pyrolysis reaction ranges from about $10^{-3}$ to 10 seconds, particularly from $10^{-2}$ to 2 seconds.

Concerning the temperature and the residence time control of said gaseous mixture between the place where the mixing is carried out and the thermal quenching, several types of reactors can be used in order to obtain the required olefins/alkanes ratio.

The following examples, which are not restricting, illustrate the various embodiments that can be carried out in order to obtain well-defined olefins/alkanes ratios from natural gas.

A preferred embodiment of the present invention involves using a fixed bed reactor. In this embodiment, the gas, which is rich in methane, is preheated at a temperature which generally does not exceed about 600° C., then it is mixed with oxygen before it is contacted in the fixed bed. The contact mass (which can be present in the form of a powder, granules, extrudates, pellets, a monolith or supported on alkaline-earth metal and/or rare-earth metal oxides and/or carbonates, on zircon, silica, alumina, quartz or on monoliths such as, for example, iolite, mullite or alpha alumina) is heated up, through the exothermicity of the oxidation reaction, at a temperature ranging from about 750° to 1,200° C. The contact mass temperature is a function of the initial temperature of the gas containing the methane-molecular oxygen mixture, of the amount and of the enthalpy of the effluent and of the methane-oxygen mixture and of the heat capacity of the effluent.

Said added gas is then introduced into the reactor after the contact bed or at a place where at least 80% (preferably at least 95%) of the molecular oxygen has been consumed. Said added gas can be introduced at room temperature or pre-heated to a temperature lower than that of the effluent. In both cases, said added gas is used for lowering the effluent temperature and it then produces a mixture the temperature of which is lower than the effluent temperature. The temperature of the mixture can be controlled by regulating the temperatures of the methane charge and of said added gas, and the initial molecular oxygen percentage. The residence time of the mixture (of effluent and said added gas) is determined in relation to the mixture temperature and the required pyrolysis severity. The pyrolysis reaction can be carried out either in the absence of a contact mass or in the presence of a contact mass (preferably on a fixed bed), such as one of those which have been previously described for the selective oxidation of methane.

Another preferred embodiment of the present invention utilizes a boiling bed reactor. In this case, the operating conditions are the same except for the contact mass (which can be present in the form of powder or granules) which remains suspended.

Another preferred embodiment of the invention uses a circulating bed or a fluidized bed reactor. In this embodiment, said methane gas is pre-heated up to a temperature which generally does not exceed about 600° C., then it is mixed up with the gas containing the molecular oxygen before it is introduced into the reactor bottom. The methane and oxygen charge draws the hot contact mass which is carried along up to the top of the reactor. The contact mass (which can be present in the form of powder or granules or supported on alkaline-earth metal and rare-earth metal oxides and/or carbonates, on zircon, silica, alumina, quartz, alpha alumina or other supports) either moves towards the reactor bottom following a different way, where it is drawn again, or it is transferred outside the reactor for a subsequent treatment, after which it is drawn again.

Said added gas is then supplied into the reactor, at a place where at least 80% of the molecular oxygen has been consumed. Said added gas can be introduced at room temperature or pre-heated at a temperature lower than that of the effluent. As above, the residence time of the mixture (of effluent and said added gas) is determined in relation to the mixture temperature and the required pyrolysis severity.

The embodiments are not limited to the examples which have been described above. In fact, the beneficial effects of adding a gas which contains at least one saturated hydrocarbon at a place where at least about 80% (preferably at least 95%) of the molecular oxygen has been consumed (through the methane selective oxidation reaction) appear whatever the form of the reactor, although the preferred forms are fixed, boiling and circulating beds.

Whatever the reactor type used, distinct reaction sections can be used for stages (2) and (4) of the process (FIG. 1) or it is possible to use only one section comprising two successive reaction zones (FIG. 2).

BRIEF DESCRIPTION OF THE DRAWINGS

The examples are illustrated by FIGS. 1 and 2.

A flow of natural gas (2) is fractionated in the separator (1) into methane (3) and superior hydrocarbons (4). The methane flow (3) is fed into a 1,300 mm high, vertical quartz tube with an inner diameter of 13 mm. The reactor is also supplied with oxygen through line (6). In the lower part of tube (5), it has been successively stacked, from the bottom up:
quartz grains (grain size: 1 to 2 mm), up to 465 mm high
a quartz wool pad (5 mm thick)
the contact bed (30 mm thick)
a second quartz wool pad
other quartz grains, in order to reach a height of 550 mm.

The ethane and superior hydrocarbons flow (7) is then added and the resulting mixture follows its way into the upper part of tube (8) (between the 550 mm and 1,300 mm levels).

Both successive sections are each set in an oven and the part of the pipe located between both ovens, which is 40 mm long, is thermally insulated.

The effluent gas is quenched (9) and carried off (10) if one wishes to use it as it is. It can also be recycled (11); it is then often advantageous to subject the gas to various fractionings such as:
purging, which helps avoid the accumulation of gases such as $H_2$, He, $N_2$ or CO;
amines washing, which allows to eliminate $CO_2$;
methanation allowing to convert CO and $H_2$ into $CH_4$ and $H_2O$.

These fractionings are globally represented by unit (12), and the separated gas is removed through line (13). The remaining gas, which contains non-converted hydrocarbons and ethylene, is sent to separator (1) through line (14).

The ($C_2$+) hydrocarbons from separator (1) are subjected to a fractioning process in unit (15), in order to remove at least the main part of the ethylene and to feed a flow rich in saturated hydrocarbons into pipe (7). Unit (15) can be any unit able to separate olefins. It may be an absorption in sulfuric acid, a distillation, an oligomerization of olefins into liquid fuels, for example into gasoline and/or gas-oil. These products are discharged through line (16).

Line 17 allows to take samples, especially in order to determine the conversion of oxygen. It should be pointed out here a variant of FIG. 1 which has shown comparable results (FIG. 2). The two sections 5 and 8 of the reaction tube are directly placed one after the other, the whole being located in a same oven.

What will be called hereafter first reactor and second reactor are respectively the oxidizing lower section (5) and the pyrolytic upper section (8) of the quartz tube described above.

EXAMPLES

In all the examples, the volume of the contact bed is 3.2 ml. The contact beds are prepared as follows:

Contact mass A: the contact mass is prepared by calcinating a mechanical mixture of $SrCO_3$ and $La_2(CO_3)_3$ in a 0.5 Sr/La atomic ratio, for two hours at 600° C., in the air. The contact bed is made of 0.3 g of contact mass diluted in 3.2 ml of tabular alumina grains (the size of which ranges from 0.3 to 0.6 mm).

Contact mass B: magnesia grains (their size ranges from 0.5 to 1 mm) are calcinated at 600° C., in the air, for two hours and are then let cool down in a drier at room temperature. After that, the grains are impregnated with an aqueous solution of $Ba(NO_3)_2$ and $La(NO_3)_3$, in a 0.5 Ba/La atomic ratio, for 1 minute at 40° C. while being stirred. Then, the supported contact mass is calcinated at 800° C. for two hours. The contact bed only contains the supported contact mass, without any diluent.

Contact mass C: the contact bed is prepared as in the case of B, but a $Sr(NO_3)_2$ and $La(NO_3)_3$ aqueous solution is used, in a 0.5 Sr/La atomic ratio.

The indicated flow rates do not take into account the other superior hydrocarbons, particularly the $C_4$ and $C_6$ hydrocarbons, which, by means of a gas analysis of the effluent, show significant concentrations.

EXAMPLES 1–4

A natural gas with a volume ratio of $C_2H_6/(C_2H_6+CH_4)=9.1\%$ and contact bed A are used.

The residence time in the contact bed of the oxidizing lower section (5) (in examples 1, 2 and 4) is about 0.044 second. This value is based on the volume (3.2 ml) and the temperature (880° C.) of the contact bed and on the gas flow rate at point 17 of example 1 (2.75 g mol/h).

In example 3, the total gas is fed through the two reactors (5, then 8), without being fractionated.

In the other cases (examples 1, 2 and 4), the gas is first fractionated into methane and ethane. In example 1, the methane is fed into reactor (5), reactor (8) is not used. In example 2, the methane is successively fed through both reactors (5, then 8); the ethane is neither used in example 1 nor in example 2.

In example 4, according to the invention, the methane is successively fed through reactors (5 and 8) and the ethane is introduced at the inlet of the second reactor (8), at a place where the oxygen conversion amounts to 99.6%. In all cases, contact bed A is used in reactor (5) with a $O_2/(O_2+CH_4)$ ratio of 9% by volume at the inlet of reactor (5).

The residence time in the pyrolytic upper section (8) of this example is about 0.79 second. The residence time is determined by means of the volume of section 8 in the oven (diameter=13 mm, height=500 mm, volume=66.4 cm$^3$) and the flow rate per second of the gas that comes out of reactor (8), at a temperature of 850° C. (total flow rate=3.28 mol/h, flow rate per second=84 cm$^3$/sec).

The operating conditions and the results after the quenching process (9) are shown in Table 1.

EXAMPLES 5-8

Examples 5-8, Table 2, are respectively carried out in the same conditions as in examples 1-4; but the $O_2/(O_2+CH_4)$ ratio is 13%. It should also be taken into account that the gaseous mixture from the pyrolysis reaction is richer in $C_2+$ products and in hydrogen when the ethane is added after the major part (99.7%) of the molecular oxygen (example 8) has been consumed.

EXAMPLES 9-16

In examples 9-16, Table 3, the reactions are carried out with contact bed B. In these examples, the bed temperature (first reactor) is maintained at 880° C. and the methane flow rate is set at 1,000 ml/mn. It appears that the olefins/alkanes ratio does not depend on the percentage of molecular oxygen in the charge and on the amount of ethane added after crossing of the contact bed, but it directly depends on the temperature in the pyrolysis oven (reactor 2). The percentage of molecular oxygen which is consumed in these examples is exactly the same at the level of the sample tube (between the two reactors) as at the outlet of the second reactor.

EXAMPLES 17-22

Examples 17-22 are carried out with contact bed C, maintaining the temperature of the bed (first reactor) at 880° C. and that of the second reactor at 850° C. and maintaining the methane flow rate at 1,000 ml/mn and the molecular oxygen flow rate at 150 ml/mn. Table 4 shows that the flow rates of molecular oxygen, carbon monoxide and carbon dioxide do not change when the flow rate of the added ethane changes.

EXAMPLE 23

Example 23 is carried out in the same conditions as those described in example 17. A naphtha cut (temperature range: 25°-130° C., paraffins percentage=81%) is added in part (7) of the reactor with a liquid flow rate of 0.2 ml/mn, after the major part (99.8%) of the molecular oxygen has been consumed. The gas analysis of the effluent shows that this one consists of 0.179 mol/h ethylene, 0.037 mol/h propylene, 0.058 mol/h ethane and 0.003 mol/h propane. The olefins/alkanes ratio for the $C_2+C_3$ products is 3.5.

TABLE 1

| | EXAMPLE | | | |
|---|---|---|---|---|
| | 1 | 2 | 3 | 4 |
| Bed temperature (1st reactor) °C. | 881 | 880 | 880 | 880 |
| 2nd reactor temperature | a | 850 | 850 | 850 |
| $CH_3$ flow rate (ml/mn) | 1,000 | 1,000 | 1,000 | 1,000 |
| $O_2$ flow rate (ml/mn) | 99 | 99 | 99 | 99 |
| $C_2H_3$ flow rate at 1st reactor inlet (ml/mn) | 0 | 0 | 100 | 0 |
| Flow rate of $C_2H_6$ introduced between the two reactors (ml/mn) | 0 | 0 | 0 | 100 |
| Flow rates (mol/h) at the outlet | | | | |
| $H_2$ | 0.064 | 0.124 | 0.222 | 0.303 |
| $O_2$ | 0.001 | 0.001 | 0.002 | 0.001 |
| CO | 0.016 | 0.017 | 0.039 | 0.018 |
| $CO_2$ | 0.060 | 0.059 | 0.064 | 0.059 |
| $C_2H_4$ | 0.066 | 0.105 | 0.204 | 0.267 |
| $C_2H_6$ | 0.082 | 0.036 | 0.067 | 0.094 |
| $C_3H_6$ | 0.004 | 0.008 | 0.012 | 0.011 |
| $C_3H_8$ | 0.004 | 0 | 0 | 0 |
| $CH_4$ | 2.104 | 2.118 | 2.319 | 2.168 |
| $H_2O$ | 0.358 | 0.359 | 0.325 | 0.358 |
| Total $C_2+$ $(C_2+C_3)$ | 0.156 | 0.149 | 0.283 | 0.372 |
| $CH_3$ conversion % | 15.8 | 15.3 | c | 15.3 d |
| $O_2$ conversion % | 99.6 | 99.6 | 99.2 | 99.6 |
| Added $C_2H_6$ converstion % | b | b | c | 76.8 d |
| olefins/$C_2+$ alkanes ratio | 0.8 | 3.1 | 3.2 | 3.0 | a - not used
b - not applicable in these cases
c - the ethane and methane conversions cannot be directly calculated
d - the methane conversion is the same as in example 2; the methane flow rate increase at the reactor outlet in example 4, compared to that in example 2, is due to the partial conversion of the ethane into methane.

TABLE 2

| | EXAMPLE | | | |
|---|---|---|---|---|
| | 5 | 6 | 7 | 8 |
| Bed temperature (1st reactor) °C. | 880 | 880 | 880 | 880 |
| 2nd reactor temperature | a | 850 | 850 | 850 |
| $CH_3$ flow rate (ml/mn) | 1,000 | 1,000 | 1,000 | 1,000 |
| $O_2$ flow rate (ml/mn) | 150 | 150 | 150 | 150 |
| $C_2H_3$ flow rate at 1st reactor inlet (ml/mn) | 0 | 0 | 100 | 0 |
| Flow rate of $C_2H_6$ introduced between the two reactors (ml/mn) | 0 | 0 | 0 | 100 |
| Flow rates at the outlet (mol/h) | | | | |
| $H_2$ | 0.093 | 0.160 | 0.243 | 0.318 |
| $O_2$ | 0.001 | 0.001 | 0.004 | 0.001 |
| CO | 0.038 | 0.041 | 0.069 | 0.043 |
| $CO_2$ | 0.105 | 0.101 | 0.109 | 0.103 |
| $C_2H_4$ | 0.091 | 0.133 | 0.219 | 0.292 |
| $C_2H_6$ | 0.091 | 0.042 | 0.066 | 0.104 |
| $C_3H_6$ | 0.005 | 0.009 | 0.013 | 0.010 |
| $C_3H_8$ | 0.003 | 0 | 0 | 0 |
| $CH_4$ | 1.969 | 1.981 | 2.213 | 2.032 |
| $H_2O$ | 0.500 | 0.505 | 0.455 | 0.499 |
| Total $C_2+$ $(C_2+C_3)$ | 0.190 | 0.184 | 0.298 | 0.406 |
| $CH_3$ conversion % | 21.2 | 20.8 | c | 20.8 d |
| $O_2$ conversion % | 99.7 | 99.7 | | 99.7 |
| Added $C_2H_6$ converstion % | b | b | c | 75.2 d |
| olefins/$C_2+$ alkanes ratio | 1.0 | 3.4 | 3.5 | 2.9 | a - not used
b - not applicable in these cases
c - the ethane and methane conversions cannot be directly calculated
d - the methane conversion is the same as in example 6; the methane flow rate increase at the reactor outlet in example 8, compared to that in example 6, is due to the partial conversion of the ethane into methane.

TABLE 3

| | EXAMPLE | | | | | | | |
|---|---|---|---|---|---|---|---|---|
| | 9 | 10 | 11 | 12 | 13 | 14 | 15 | 16 |
| 2nd reactor temperature °C. | 850 | 850 | 880 | 880 | 850 | 850 | 880 | 880 |
| $O_2$ flow rate (ml/mn) | 150 | 150 | 150 | 150 | 99 | 99 | 99 | 99 |

TABLE 3-continued

| | EXAMPLE | | | | | | | |
|---|---|---|---|---|---|---|---|---|
| | 9 | 10 | 11 | 12 | 13 | 14 | 15 | 16 |
| Flow rate of $C_2H_6$ introduced between the two reactors (ml/mn) | 50 | 100 | 50 | 100 | 50 | 100 | 50 | 100 |
| Flow rate at outlet (mol/h) | | | | | | | | |
| $H_2$ | 0.218 | 0.310 | 0.274 | 0.387 | 0.199 | 0.299 | 0.255 | 0.366 |
| $O_2$ | 0.001 | 0.001 | 0.001 | 0.001 | 0.001 | 0.001 | 0.001 | 0.001 |
| CO | 0.021 | 0.020 | 0.020 | 0.020 | 0.010 | 0.011 | 0.011 | 0.011 |
| $CO_2$ | 0.114 | 0.112 | 0.112 | 0.113 | 0.060 | 0.060 | 0.060 | 0.59 |
| $C_2H_4$ | 0.211 | 0.297 | 0.223 | 0.320 | 0.188 | 0.277 | 0.200 | 0.294 |
| $C_2H_6$ | 0.071 | 0.106 | 0.036 | 0.050 | 0.066 | 0.095 | 0.032 | 0.046 |
| $C_3H_6$ | 0.012 | 0.012 | 0.014 | 0.014 | 0.012 | 0.013 | 0.014 | 0.016 |
| $O_2$ conversion % (17) | 99.7 | 99.7 | 99.7 | 99.7 | 99.6 | 99.6 | 99.6 | 99.6 |
| olefins/$C_2+$ alkanes ratio | 3.1 | 2.9 | 6.6 | 6.7 | 3.0 | 3.1 | 6.7 | 6.7 |

TABLE 4

| | EXAMPLE | | | | | |
|---|---|---|---|---|---|---|
| | 17 | 18 | 19 | 20 | 21 | 22 |
| Flow rate of $C_2H_6$ introduced between the 2 reactors (ml/mn) | 0 | 11.1 | 23.3 | 47.9 | 71.4 | 93.4 |
| Flow rate at outlet (mol/h) | | | | | | |
| $H_2$ | 0.118 | 0.136 | 0.156 | 0.202 | 0.247 | 0.287 |
| $O_2$ | 0.001 | 0.001 | 0.001 | 0.001 | 0.001 | 0.001 |
| CO | 0.022 | 0.022 | 0.022 | 0.022 | 0.022 | 0.022 |
| $CO_2$ | 0.112 | 0.112 | 0.112 | 0.112 | 0.112 | 0.112 |
| $C_2H_4$ | 0.122 | 0.139 | 0.157 | 0.200 | 0.244 | 0.280 |
| $C_2H_6$ | 0.039 | 0.048 | 0.058 | 0.073 | 0.091 | 0.104 |
| $C_3H_6$ | 0.008 | 0.010 | 0.011 | 0.011 | 0.012 | 0.012 |
| $O_2$ conversion % (17) | 99.7 | 99.7 | 99.7 | 99.7 | 99.7 | 99.7 |
| olefins/$C_2+$ alkanes ratio | 3.3 | 3.1 | 2.9 | 2.9 | 2.8 | 2.8 |

We claim:

1. A process for producing olefins from natural gas containing methane and ethane, comprising:
   (a) separating the natural gas into two fractions, a first methane-enriched gas fraction and a second ethane-enriched gas fraction,
   (b) oxidizing the first gas fraction with molecular oxygen, in the presence of a contact mass allowing the oxidizing coupling of the methane into superior hydrocarbons,
   (c) mixing the effluent from stage (b) with the ethane-enriched gas fraction from stage (a), when at least about 80% by volume of the molecular oxygen has been already consumed in stage (b), and
   (d) pyrolizing the mixture resulting from stage (c) to obtain a mixture containing corresponding olefins.

2. A process according to claim 1 wherein, in stage (b), the methane-enriched gas fraction from stage (a) is mixed with water steam.

3. A process according to claim 1 wherein, in stage (c), the ethane-enriched gas fraction from stage (a) is mixed with one or several saturated hydrocarbons from a source other than the natural gas.

4. A process according to claim 1 wherein, in stage (c), the ethane-enriched gas fraction from stage (a) is mixed with one or several non-hydrocarbon gases.

5. A process according to claim 1 wherein stages (b), (c) and (d) are performed in a contact mass circulating fluidized bed reactor.

6. A process according to claim 1 wherein stages (b), (c) and (d) are performed in a contact mass boiling bed reactor.

7. A process according to claim 1 wherein stage (b) is performed in a contact mass fixed bed reactor.

8. A process according to claim 1 wherein stage (b) and at least one of stages (c) and (d) are performed in a contact mass fixed bed reactor.

9. A process according to claim 7 wherein the contact mass in the fixed bed is supported on a monolith.

10. A process according to claim 7 wherein the contact mass in the fixed bed is in the form of a monolith.

11. A process according to claim 1, wherein the contact mass corresponds to the formula $T_aLn_2O_{b-c}(CO_3)_c$, wherein T represents at least one alkaline-earth metal, Ln represents at least one rare-earth metal, $a=0.001$ to 1,000, $b=3+a$, and $c=0.1$ to b.

12. A process according to claim 1, wherein the contact mass corresponds to the formula $T_aM_dLn_2O_{e-f}(CO_3)_f$, wherein T represents at least one alkaline-earth metal, M represents at least one metal from Group IVa, Ln represents at least one rare-earth metal, $a=0.001$ to 1,000, $d=0.001$ to 2, $e=3+a+2d-z$, $f=0.1$ to e, and $z=0$ to 0.5 d.

13. A process according to claim 1, wherein the contact mass is produced by mixing magnesia with a lanthanum compound and a barium or strontium compound.

14. A process according to claim 1, wherein the contact mass is produced by impregnating magnesia with an aqueous solution of lanthanum nitrate and barium or strontium nitrate.

15. A process according to claim 1, wherein the effluent from stage (d) is fractionated so as to eliminate carbon dioxide, subjected to a methanation treatment in order to convert CO and $H_2$ into $CH_4$ and $H_2O$ and the resulting gaseous effluent is sent to stage (a).

* * * * *